United States Patent [19]
Guentensberger et al.

[11] Patent Number: 5,952,003
[45] Date of Patent: *Sep. 14, 1999

[54] TERAZOSIN CAPSULES

[75] Inventors: Jeffrey W. Guentensberger, Northglenn; Christopher L. Pelloni, Louisville, both of Colo.

[73] Assignee: Novartis Corporation, Summit, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/691,907

[22] Filed: Aug. 1, 1996

[51] Int. Cl.⁶ ...................................................... A61K 9/48
[52] U.S. Cl. ........................... 424/451; 424/489; 424/490
[58] Field of Search .................................... 424/451, 489, 424/490; 514/254; 544/291

[56] References Cited

U.S. PATENT DOCUMENTS

| | | | |
|---|---|---|---|
| 4,092,315 | 5/1978 | Bianco | 544/291 |
| 4,112,097 | 9/1978 | Winn et al. | 424/257 |
| 4,251,532 | 2/1981 | Roteman | 424/251 |
| 5,122,514 | 6/1992 | Boger et al. | 514/19 |
| 5,212,176 | 5/1993 | Kyncl et al. | 514/254 |
| 5,294,615 | 3/1994 | Meyer et al. | 514/254 |
| 5,362,730 | 11/1994 | Bauer et al. | 514/254 |
| 5,412,095 | 5/1995 | Morley et al. | 544/291 |
| 5,504,207 | 4/1996 | Mannino et al. | 544/291 |
| 5,587,377 | 12/1996 | Patel et al. | 514/254 |

FOREIGN PATENT DOCUMENTS

WO 93/19758 10/1993 WIPO .

OTHER PUBLICATIONS

Information obtained under The Freedom of Information Act relating to NDA 20–347 (Dec. 1994).

*Primary Examiner*—Thurman K. Page
*Assistant Examiner*—William E. Benston, Jr.
*Attorney, Agent, or Firm*—George R. Dohmann

[57] ABSTRACT

A capsule dosage form containing solid form of terazosin in a solid carrier is disclosed. The capsule dosage form is stable under accelerated stability conditions and therapeutically equivalent to known liquid-filled terazosin capsules.

17 Claims, No Drawings

5,952,003

TERAZOSIN CAPSULES

SUMMARY

Terazosin is administered to subjects in filled gelatin capsules containing a solid fill. The capsules are bioequivalent to a reference liquid-filled terazosin capsule dosage form, but have an advantageous shelf life and are simpler to manufacture.

BACKGROUND

Terazosin, especially in its salt forms, is a well-known medicament which is useful in the treatment of hypertension and benign prostatic hyperplasia. For example, U.S. Pat. No. 4,026,894 discloses the hydrochloride salt of terazosin as well as its use in pharmaceutical formulations used for the treatment of hypertension, and U.S. Pat. No. 4,251,532 discloses the compound terazosin hydrochloride dihydrate and its use as a pharmaceutical active ingredient.

The U.S. Food and Drug Administration (FDA) first approved terazosin hydrochloride dihydrate for sale in the United States in 1987 as a tablet formulation which was marketed by Abbott Laboratories under the tradename HYTRIN.

U.S. Pat. No. 5,294,615 describes a soft gelatin capsule dosage form containing terazosin hydrochloride in a non-aqueous liquid carrier and indicates that polyethylene glycol is a preferred non-aqueous liquid carrier. In 1994, the FDA approved a soft gelatin capsule formulation containing the active ingredient suspended in a non-aqueoLs liquid carrier composed primarily of polyethylene glycol with some glycerine present.

The present invention relates to the surprising discovery that a stable, therapeutic equivalent of known liquid-filled capsule dosage forms of terazosin hydrochloride is prepared simply and effectively by replacing the liquid carrier with a solid carrier. Thus, the present invention relates to solid-filled terazosin hydrochloride capsules which are stable under accelerated conditions and which are therapeutic equivalents of the liquid-filled capsule dosage forms.

As therapeutic equivalents, the inventive solid-filled terazosin hydrochloride capsules are surprisingly bioequivalent to the FDA approved liquid-filled terazosin hydrochloride capsules. It is a great advantage that the inventive formulations are bioequivalent to the FDA approved liquid-filled terazosin hydrochloride capsules because the inventive formulations can be marketed as generic equivalents of the approved product without performing new safety and efficacy studies, which add considerably to the cost of obtaining FDA approval to market a drug product.

DETAILED DESCRIPTION

The present invention relates to a pharmaceutical capsule dosage form which comprises a pharmaceutically effective amount of terazosin in the form of a solid pharmaceutically acceptable salt, or solvate thereof, and a solid carrier, which capsule dosage form is bioequivalent to a reference terazosin capsule, which reference terazosiin capsule is a liquid-filled capsule comprising an equivalent amount of terazosin and a non-aqueous liquid carrier. Thus, the present invention relates to an improved, pharmaceutical capsule dosage form containing terazosin, in the form of a salt or solvate thereof, which dosage form is bioequivalent to a liquid-filled terazosin capsule comprising an equivalent amount of terazosin and a nonaqueous liquid carrier, wherein the improvement consists essentially of replacing the nonaqueous liquid carrier with a pharmaceutically acceptable carrier which is a solid at 25° C.

In particular, the present invention relates to a pharmaceutical capsule dosage form which is stable under accelerated stability conditions. Accordingly, the present invention relates to a stable pharmaceutical solid-filled capsule dosage form which comprises a pharmaceutically effective amount of terazosin in the form of a solid pharmaceutically acceptable salt, or solvate thereof, and a solid carrier, which solid-filled capsule dosage form is therapeutically equivalent to a reference liquid-filled terazosin capsule comprising an equivalent amount of terazosin and a non-aqueous liquid carrier, and which solid-filled capsule dosage form has an average dissolution at 30 minutes measured according to U.S.P. Method II at 50 r.p.m. in water of at least 85 percent of the label amount with no individual capsule below 80 percent of the label amount after being maintained in a high density polyethylene bottle closed with a screw cap at about 40° C. and 85 percent relative humidity for twelve weeks.

Pharmaceutical capsule dosage forms are well-known in the art. In general, a capsule dosage form consists essentially of a shell and a fill, which is encapsulated by the shell and contains the active ingredient, in this case terazosin in the form of a salt or solvate, as well as carrier. The shell is usually primarily composed of gelatin and can contain additional ingredients such as a plasticizer, like glycerine, sorbitol or propylene glycol, an opacifier, a coloring agent, a flavoring agent and/or a preservative. Generally, capsule shells are classified as either soft elastic capsules, such as those described in U.S. Pat. No. 5,294,615 which have a plasticizer, or hard capsule shells, which generally do not contain any appreciable amount of a plasticizer. Preferably, the inventive dosage forms have a hard capsule shell due to the relative ease of manufacture.

In this application, when referring to a solid-filled capsule dosage form, "stable" means that the capsule dosage form has an expiration date which permits it to be sold for a period of at least two years from its manufacture.

A pharmaceutically effective amount of terazosin is an amount which is appropriate in a dosage form useful to treat hypertension or benign prostate hyperplasia. In general, from 1 to 15 mg of terazosin is a pharmaceutically effective amount. Currently, terazosin hydrochloride is marketed in dosage forms containing 1, 2, 5, and 10 mg equivalent of terazosin.

Solid pharmaceutically acceptable salts and solvates of terazosin include any non-toxic acid addition salt which is water-soluble and solid at room temperature, in particular the hydrochloride salt in anhydrous form, including polymorphic forms and nixtures thereof, or as a non-toxic solvate, such as terazosin hydrochloride dihydrate.

In this application, the expression "therapeutically equivalent to a reference liquid-filled terazosin capsule" is intended to mean that the inventive capsule dosage form is a generic equivalent of the reference liquid-filled terazosin capsule and as such is rated an AB therapeutic equivalent of the reference liquid-filled capsule by the FDA whereby actual or potential bioequivalence problems have been resolved with adequate in vivo and/or in vitro evidence supporting bioequivalence. Accordingly, the solid-filled capsule dosage form is the subject of an Abbreviated New Drug Application (ANDA) filed under section 505(j) of the Food Drug and Cosmetic Act (FDCA) (21 U.S.C. 355(j)) which contains a bioequivalence study wherein the reference drug is a liquid-filled terazosin capsule containing the active ingredient dissolved or suspended in a non-aqueous liquid carrier as the fill.

The expression "bioequivalent" or "bioequivalence" is a term of art and is intended to be defined in accordance with

*Approved Drug Products with Therapeutic Equivalence Evaluations*, 15th Edition, pages vii–xvii, which is published by the U.S. Department of Health and Human Services, and is commonly known as the "Orange Book". Bioequivalence of different formulations of the same drug substance involves equivalence with respect to the rate and extent of drug absorption. The extent and rate of absorption of the test formulation is compared to a reference formulation in order to determine whether the two formulations are bioequivalent. The standard bioequivalence study is conducted in crossover fashion by extensive testing which includes administering single doses of the test and reference drugs to a number of volunteers, usually 12 to 24 healthy normal adults, and then measuring the blood or plasma levels of the drug over time. The pharmacokinetic characteristics of the concentration-time curve, such as the maximum observed plasma concentration ($C_{max}$), the time to reach $C_{max}$, and the area under the plasma concentration versus time curve (AUC), are examined by statistical procedures which are well-established in the field of pharmacokinetics. Two formulations whose rate and extent of absorption differ by −20%/+25% or less are generally considered to be bioequivalent. Detailed guidelines for establishing the bioequivalence of a formulation with a reference formulation have been published by the FDA Office of Generic Drugs, Division of Bioequivalence.

The expression "solid carrier" means that the overall physical form of the filling of the capsule is in solid form at room temperature. Generally, the filling is a powder which has been formed into a capsule-shaped slug at low compression.

The expression "liquid-filled" means that the overall physical form of the filling is a liquid at room temperature. The expression "liquid-filled" is intended to include suspensions or mixtures of liquids and solids which have the overall characteristics of a liquid.

An "equivalent amount of terazosin" means the same amount of terazosin base. Thus, by weight, it requires less anhydrous terazosin hydrochloride than terazosin hydrochloride dihydrate to have an equivalent amount of terazosin. Generally, the inventive capsules have an equivalent amount of terazosin of 1 mg, 2 mg, 5 mg or 10 mg.

The expression "non-aqueous liquid carrier" is defined according to U.S. Pat. No. 5,294,615, which is here incorporated by reference. In general, liquid carriers containing a major portion a liquid polyethylene glycol, for example, those having a molecular weight between about 200 and about 600, alone or combined with additives, like a viscosity-building agent or glycerine, are described as suitable non-aqueous liquid carriers.

The present solid-filled capsule dosage form is stable based on accelerated stability studies. Accelerated stability studies are well-known in the pharmaceutical formulation sciences. In general, the capsules are maintained at about 40° C. and 85 percent relative humidity for up to twelve weeks in a high density polyethylene (HDPE) bottle closed with a screw cap and the release rate of the capsule is measured by in vitro dissolution testing. Since accelerated stability studies are generally predictive of the stability of a formulation under normal conditions, for example, by use of the Arrhenius rate equation, such studies are used to determine the appropriate expiration dating for the formulation. If the formulation performs well in accelerated stability studies, no further testing is usually required to establish an advantageous expiration period. If the dissolution slows significantly after storage, the accelerated stability study does not support an advantageous expiration period. In general, it is a great advantage if an expiration period of at least 24 months is established by an accelerated stability study.

In general, the average dissolution at 30 minutes measured according to U.S.P. Method II at 50 r.p.m. in water for 6 randomly selected capsules of the present invention, which capsules were maintained at about 40° C. and 85 percent relative humidity for twelve weeks in a high density polyethylene (HDPE) bottle closed with a screw cap, is at least 85 percent of the label amount, with no individual capsule below 80 percent of the label amount, the label amount being the amount of terazosin base listed on the label, for example, a 5 mg capsule has a label amount of 5 mg of terazosin. Preferably, the average dissolution at 30 minutes is at least 90 percent of the label amount with no individual capsule below 80, preferably 85, percent of the label amount. Most preferably, the average dissolution at 30 minutes is at least 90, preferably 95, percent of an initial dissolution; the initial dissolution being the result obtained by testing capsules from the same lot under identical conditions; except that the initially tested capsules are not subjected to accelerated stability conditions. Thus, the average. dissolution of the inventive capsule dosage form remains virtually constant over time, even after being stored under accelerated conditions for 12 weeks. Capsules showing the results described above in accelerated stability studies are generally expected to be stable under normal conditions for at least two years.

The present solid-filled capsules are bioequivalent to a reference liquid-jilled terazosin capsule comprising an equivalent amount of terazosin and a non-aqueous liquid carrier. Preferably, the liquid carrier comprises a major portion, such as 80 to 100% by weight, of a liquid polyethylene glycol, such as is described in U.S. Pat. No. 5,294,615, especially wherein the liquid carrier further comprises a minor amount, such as from 1 to 4 weight-percent, of glycerine. Most preferably, the reference liquid-filled terazosin capsule is a terazosin hydrochloride capsule which is the subject of a New Drug Application which is approved by the U.S. Food and Drug Administration, especially New Drug Application number N20347, which was approved on Dec. 14, 1994.

In general, the solid carrier is composed of a solid diluent along with other optional ingredients such as a disintegrant, a lubricant, a binder or a surfactant. A solid carrier used in the inventive formulations is typically composed of (a) from 70 to 100 percent by weight of a diluent; and optionally an effective disintegration-producing amount of a disintegrant and/or an effective lubricating amount of a lubricant. For example a typical formulation contains (a) from 70 to 100 percent by weight of a diluent, (b) from 0 to 30 percent by weight of a disintegrant; and (c) 0 to 10 percent by weight of a lubricant. Preferably, the solid carrier contain (a) from 85 to 97 percent by weight of a diluent; (b) from 1 to 10 percent by weight of a disintegrant; and (c) 0.2 to 5 percent by weight of a lubricant. Most preferably, the solid carrier contains (a) from 90 to 97 percent by weight of a diluent; (b) from 1 to 5 percent by weight of a disintegrant; and (c) 0.5 to 2 percent by weight of a lubricant.

Any pharmaceutically acceptable solid diluent which is non-toxic, inert, both to the active ingredient and to the capsule shell, and compressible is useful in the solid carrier. Preferably, the diluent is readily wetted by or dissolved in an aqueous medium. In general, the diluent is a non-toxic, inert monosaccharide, disaccharide, polysaccharide, solid fatty acid, solid triglyceride, or solid phosphate, carbonate, silicate, sulfate or chloride salt. Suitable saccharide diluents include anhydrous or hydrated lactose, microcrystalline cellulose, sucrose, dextrose, sorbitol, manitol, and starch. Suitable inorganic diluents include dibasic calcium phosphate, calcium sulfate, kaolin, magnesium carbonate, magnesium oxide, talc, potassium chloride and sodium chloride and/or hydrates thereof.

Disintegrants and lubricants are well-known in the pharmaceutical sciences. Suitable disintegrants include starch, croscarmellose sodium, crospovidone, sodium starch glycolate, croscarmellose calcium, microcrystalline cellulose and polacralin potassium, and the like. Suitable lubricants include magnesium stearate, sodium stearyl fumarate, hydrogenated vegetable oil, hydrogenated castor oil, hydrogenated cottonseed oil, stearic acid and calcium stearate, and the like.

It is possible for certain ingredients to serve more than one function in the formulation, for example, microcrystalline cellulose and starch each function as both diluent and as a disintegrant.

In addition to the diluent, disintegrant and lubricant, solid carriers accorcing to the present invention can also include a binder, such as povidone, hydroxypropyl methylcellulose, hydroxypropyl cellulose, hydroxyethyl cellulose, ethylcellulose and sodium alginate, as well as other pharmaceutical excipients, such as glidants and surfactants, like talc, colloidal silicon dioxide, polyethylene glycol, sodium lauryl sulfate, polysorbate, docusate sodium.

It is important for the solid carrier to contain only excipients which are ineart to both the active ingredient and to the capsule shell. With regard to the capsule shell, inert excipients are those which do not promote cross-linking in the capsule shell. Such cross-linking producing excipients are well-known in the pharmaceutical formulation sciences and are generally those which degrade by releasing formaldehyde. Thus, the inert solid carrier is a non-formaldehyde-releasing solid carrier.

The present invention further relates to a method of administering a therapeutically effective amount of terazosin to a human subject, which comprises producing a plasma concentration of terazosin in the subject having both a maximum concentration ($C_{max}$) and an area under a plasma-concentration vs. time curve (AUC) within the range from −20% to +25% of that produced by a reference liquid-filled terazosin capsule, which contains an equivalent amount of terazosin in a non-aqueous liquid carrier, by administering a solid-filled capsule dosage form which consists essentially of a pharmaceutically effective amount of terazosin in the form of a solid pharmaceutically acceptable salt, or solvate thereof, and a solid carrier to the subject; especially wherein the reference capsule is the subject of approved New Drug Application number N20347. Preferably, the terazosin is present in the form of anhydrous terazosin hydrochloride or terazosin hydrochloride dihydrate.

In addition, the present invention relates to a method of formulating a stable therapeutic equivalent of a reference liquid-filled terazosin capsule, which comprise, the steps of (a) preparing a solid-filled capsule dosage form consisting essentially of a pharmaceutically effective amount of terazosin in the form of a solid pharmaceutically acceptable salt, or solvate thereof, and a solid carrier, which solid-filled capsule dosage form has an average dissolution at 30 minutes measured according to U.S.P. Method 11 at 50 r.p.m. in water of at least 85 percent of the label amount with no individual capsule below 80 percent of the label amount after being maintained in a high density polyethylene bottle closed with a screw cap at about 40° C. and 85 percent relative humidity for twelve weeks; and (b) establishing that the solid-filled capsule dosage form is a therapeutic equivalent of the reference liquid-filled terazosin capsule by conducting a bioequivalence study which demonstrates that administration of the solid-filled capsule dosage form to a human subject produces both a maximum concentration ($C_{max}$) and an area under a pleisma-concentration vs. time curve (AUC) within the range from −20% to +25% of that produced by the reference liquid-filled terazosin capsule.

The following examples further illustrate, but do not limit, the present invention.

EXAMPLE 1

Capsules containing 5 mg of terazosin were prepared by blending the following ingredients according to standard methods and encapsulating the formulation in #3 gelatin capsules.

| Ingredient | mg/dose |
|---|---|
| Terazosin HCl Anhydrous | 5.471 |
| Lactose Monohydrate, NF | 174.529 |
| Microcrystalline Cellulose, NF | 28.000 |
| Crospovidone, NF | 14.000 |
| Magnesium Stearate, NF | 3.000 |
| Total Capsule Fill Weight | 225.000 |

The rate and extent of terazosin absorption under fasting conditions of the capsules described above was compared with the rate and extent of terazosin absorption of the FDA-approved terazosin hydrochloride capsule containing the equivalent amount of terazosin base (approved on Dec. 14, 1994 under application N20347 and sold by Abbott Laboratories under the tradename HYTRIN Capsules, 5 mg) measured under identical conditions in a single dose, randomized, two-period, two-treatment, two-sequence crossover study in a group of healthy adult male volunteers. The study demonstrates that the above-described capsule formulation is bioequivalent to the liquid-filled FDA-approved capsule containing the equivalent amount of terazosin base in accordance with *Guidance Statistical Procedures for Bioequivalence Studies Using a Standard Two Treatment Crossover Design* prepared by the FDA Division of Bioequivalence because it meets the log transformed confidence intervals of 0.8–1.25 for both AUC and $C_{max}$. In vitro studies further demonstrate that capsules similar to those described above containing 1 mg, 2 mg and 10 mg of terazosin base are also bioequivalent to with the FDA-approved terazosin hydrochloride capsule containing the equivalert amount of terazosin base. The 1 mg, 2 mg and 10 mg capsules contain the above ingredients in the amounts stated above, but adjust the amount of terazosin and lactose monohydnate according to the formula terazosin HCI+ lactose monohydrate≈180 mg.

EXAMPLE 2

Capsules prepared according to Example 1 were subjected to an accelerated stability study wherein HDPE bottles containing 100 or 1000 capsules were closed with a screw cap and stored at 40° C. and 85% relative humidity for a period of from 1 to 12 weeks. After the storage period, a sample of capsules was subjected to dissolution testing according to U.S.P. Method II (paddles) at 50 rpm in 900 ml of water for 30 minutes. The average results are reported in the following table.

TABLE 1

Accelerated Stability
Dissolution Test (% of label - average of 6 capsules)

| bottle count | 1 mg 100 | 1 mg 1000 | 2 mg 100 | 2 mg 1000 | 5 mg 100 | 5 mg 1000 | 10 mg 100 | 10 mg 1000 |
|---|---|---|---|---|---|---|---|---|
| initial | 102 | 102 | 100 | 100 | 100 | 100 | 99 | 99 |
| 4 week | 105 | 105 | 98 | 98 | 99 | 101 | 98 | 99 |
| 8 week | 99 | 100 | 100 | 98 | 100 | 100 | 100 | 98 |
| 12 week | 99 | 99 | 100 | 101 | 100 | 101 | 98 | 98 |

No individual capsule showed a dissolution below 95% at 4 weeks, 91% at 8 weeks, and 88% at 12 weeks.

The accelerated stability study supports a two year expiration date for the solid-filled capsules described above.

EXAMPLE 3

The following formulations for capsules containing terazosin hydrochloride equivalent to 5 mg of terazosin are prepared by blending the ingredients according to standard methods. Capsules containing 1 mg, 2 mg and 10 mg of terazosin are prepared by encapsulating a proportional amount of the capsule fill.

| Ingredient | mg/dose |
|---|---|
| 1A. | |
| Terazosin HCl Anhydrous | 5.471 |
| Lactose Monohydrate, NF | 88.529 |
| Microcrystalline Cellulose, NF | 89.000 |
| Crospovidone, NF | 14.000 |
| Magnesium Stearate, NF | 3.000 |
| Total Capsule Fill Weight | 200.000 |
| 1B. | |
| Terazosin HCl Anhydrous | 5.471 |
| Microcrystalline Cellulose, NF | 167.529 |
| Crospovidone, NF | 14.000 |
| Magnesium Stearate, NF | 3.000 |
| Total Capsule Fill Weight | 190.000 |
| 1C. | |
| Terazosin HCl Anhydrous | 5.471 |
| Lactose Monohydrate, NF | 174.529 |
| Microcrystalline Cellulose, NF | 28.000 |
| Sodium Starch Glycolate, NF | 14.000 |
| Magnesium Stearate, NF | 3.000 |
| Total Capsule Fill Weight | 225.000 |
| 1D. | |
| Terazosin HCl Anhydrous | 5.471 |
| Lactose Monohydrate, NF | 174.529 |
| Microcrystalline Cellulose, NF | 28.000 |
| Croscarmellose Sodium, NF | 14.000 |
| Magnesium Stearate, NF | 3.000 |
| Total Capsule Fill Weight | 225.000 |
| 1E. | |
| Terazosin HCl Anhydrous | 5.471 |
| Lactose Monohydrate, NF | 170.529 |
| Microcrystalline Cellulose, NF | 28.000 |
| Crospovidone, NF | 14.000 |
| Colloidal Silicon Dioxide, NF | 2.000 |
| Talc USP | 2.000 |
| Magnesium Stearate, NF | 3.000 |
| Total Capsule Fill Weight | 225.000 |
| 1F. | |
| Terazosin HCl Anhydrous | 5.471 |
| Corn Starch, NF, Pregelatinized | 174.529 |
| Microcrystalline Cellulose, NF | 28.000 |
| Crospovidone, NF | 14.000 |
| Magnesium Stearate, NF | 3.000 |
| Total Capsule Fill Weight | 225.000 |
| 1G. | |
| Terazosin HCl Anhydrous | 5.471 |
| Lactose Monohydrate, NF | 172.529 |
| Microcrystalline Cellulose, NF | 28.000 |
| Crospovidone, NF | 14.000 |
| Sodium Stearyl Fumarate, NF | 5.000 |
| Total Capsule Fill Weight | 225.000 |
| 1H. | |
| Terazosin HCl Anhydrous | 5.471 |
| Dibasic Calcium Phosphate USP | 199.529 |
| Microcrystalline Cellulose, NF | 28.000 |
| Crospovidone, NF | 14.000 |
| Magnesium Stearate, NF | 3.000 |
| Total Capsule Fill Weight | 250.000 |
| 1I. | |
| Terazosin HCl Anhydrous | 5.471 |
| Lactose Monohydrate, NF | 194.529 |
| Hydroxypropyl Methylcellulose | 8.000 |
| Crospovidone, NF | 14.000 |
| Magnesium Stearate, NF | 3.000 |
| Total Capsule Fill Weight | 225.000 |
| 1J. | |
| Terazosin HCl Anhydrous | 5.471 |
| Lactose Monohydrate, NF | 197.529 |
| Povidone USP | 5.000 |
| Crospovidone, NF | 14.000 |
| Magnesium Stearate, NF | 3.000 |
| Total Capsule Fill Weight | 225.000 |
| 1K. | |
| Terazosin HCl Anhydrous | 5.471 |
| Lactose Monohydrate, NF | 170.529 |
| Microcrystalline Cellulose, NF | 28.000 |
| Crospovidone, NF | 14.000 |
| Sodium Lauryl Sulfate USP | 2.000 |
| Polyethylene Glycol, NF | 2.000 |
| Hydrogenated Vegetable Oil NF | 3.000 |
| Total Capsule Fill Weight | 225.000 |
| 1L. | |
| Terazosin HCl Anhydrous | 5.471 |
| Compressible, Sugar, NF | 194.529 |
| Microcrystalline Cellulose, NF | 28.000 |
| Crospovidone, NF | 14.000 |
| Magnesium Stearate, NF | 3.000 |
| Total Capsule Fill Weight | 245.000 |
| 1M. | |
| Terazosin HCl Anhydrous | 5.471 |
| Compressible Sugar, NF | 88.529 |
| Confectioners Sugar, NF | 89.000 |
| Crospovidone, NF | 14.000 |
| Magnesium Stearate, NF | 3.000 |
| Total Capsule Fill Weight | 200.000 |
| 1N. | |
| Terazosin HCl Anhydrous | 5.471 |
| Manitol, NF | 167.529 |

| Ingredient | mg/dose |
|---|---|
| Crospovidone, NF | 14.000 |
| Magnesium Stearate, NF | 3.000 |
| Total Capsule Fill Weight | 190.000 |
| 1O. | |
| Terazosin HCl Anhydrous | 5.471 |
| Dextrose, USP | 174.529 |
| Microcrystalline Cellulose, NF | 28.000 |
| Sodium Starch Glycolate, NF | 14.000 |
| Magnesium Stearate, NF | 3.000 |
| Total Capsule Fill Weight | 225.000 |
| 1P. | |
| Terazosin HCl Anhydrous | 5.471 |
| Lactose Monohydrate, NF | 174.529 |
| Microcrystalline Cellulose, NF | 28.000 |
| Croscarmellose Calcium, NF | 14.000 |
| Magnesium Stearate, NF | 3.000 |
| Total Capsule Fill Weight | 225.000 |
| 1Q. | |
| Terazosin HCl Anhydrous | 5.471 |
| Lactose Monohydrate, NF | 168.529 |
| Microcrystalline Cellulose, NF | 30.000 |
| Polacrallin Potassium | 14.000 |
| Magnesium Stearate, NF | 3.000 |
| Total Capsule Fill Weight | 225.000 |
| 1R. | |
| Terazosin HCl Anhydrous | 5.471 |
| Confectioners Sugar, NF | 174.529 |
| Microcrystalline Cellulose, NF | 28.000 |
| Crospovidone, NF | 14.000 |
| Magnesium Stearate, NF | 3.000 |
| Total Capsule Fill Weight | 225.000 |
| 1S. | |
| Terazosin HCl Anhydrous | 5.471 |
| Manitol, USP | 172.529 |
| Microcrystalline Cellulose, NF | 28.000 |
| Crospovidone, NF | 14.000 |
| Sodium Stearyl Fumarate, NF | 5.000 |
| Total Capsule Fill Weight | 225.000 |
| 1T. | |
| Terazosin HCl Anhydrous | 5.471 |
| Manitol, NF | 199.529 |
| Microcrystalline Cellulose, NF | 28.000 |
| Crospovidone, NF | 14.000 |
| Magnesium Stearate, NF | 3.000 |
| Total Capsule Fill Weight | 250.000 |
| 1U. | |
| Terazosin HCl Anhydrous | 5.471 |
| Sorbitol, USP | 194.529 |
| Hydroxypropyl Methylcellulose | 8.000 |
| Crospovidone, NF | 14.000 |
| Magnesium Stearate, NF | 3.000 |
| Total Capsule Fill Weight | 225.000 |
| 1V. | |
| Terazosin HCl Anhydrous | 5.471 |
| Sorbitol, USP | 197.529 |
| Povidone USP | 5.000 |
| Crospovidone, NF | 14.000 |
| Magnesium Stearate, NF | 3.000 |
| Total Capsule Fill Weight | 225.000 |
| 1W. | |
| Terazosin HCl Anhydrous | 5.471 |
| Lactose Monohydrate, NF | 170.529 |
| Microcrystalline Cellulose, NF | 28.000 |
| Sodium Alginate | 16.000 |
| Hydrogenated Castor Oil | 5.000 |
| Total Capsule Fill Weight | 225.000 |

An accelerated stability study supports an expiration period of at least two years for each of the formulations. After a single dose to a healthy human subject, each of the above formulations produces a plasma concentration of terazosin in the subject having both $C_{max}$ and an AUC within the range from −20% to +25% of that produced by a reference liquid-filled terazosin capsule.

We claim:

1. A pharmaceutical solid-filled capsule dosage form containing a fill which consists of a pharmaceutically effective amount of terazosin in the form of a solid pharmaceutically acceptable salt, or a solvate thereof, and a solid carrier, which solid-filled capsule dosage form is therapeutically equivalent to a reference liquid-filled terazosin capsule containing a liquid fill which consists of an equivalent amount of terazosin and a non-aqueous liquid carrier, and which solid-filled capsule dosage form has an average dissolution at 30 minutes for six capsules when tested according to U.S.P. Method II at 50 r.p.m. in water of at least 85 percent of the label amount with no individual capsule below 80 percent of the label amount after being maintained in a high density polyethylene bottle closed with a screw cap at about 40° C. and 85 percent relative humidity for twelve weeks.

2. A capsule dosage form of claim 1 wherein the terazosin is present as anhydrous terazosin hydrochloride or terazosin hydrochloride dihydrate.

3. A capsule dosage form of claim 2 wherein the average dissolution at 30 minutes is at least 90 percent of the label amount with no individual capsule below 80 percent of the label amount.

4. A capsule dosage form of claim 2 wherein the average dissolution at 30 minutes is at least 95 percent of an initial average dissolution.

5. A dosage form of claim 2 wherein the reference terazosin capsule comprises a liquid polyethylene glycol as the non-aqueous liquid carrier.

6. A dosage form of claim 5 wherein the non-aqueous liquid carrier further comprises from 1 to 4 percent by weight, based on the total weight of the capsule fill, of glycerine.

7. A dosage form of claim 2 wherein the reference terazosin capsule is a liquid-filled terazosin hydrochloride capsule which is the subject of a U.S. Food and Drug Administration approved New Drug Application.

8. A dosage form of claim 7 wherein the reference terazosin capsule is a liquid-filled terazosin hydrochloride capsule which is the subject of approved New Drug Application number N20347.

9. A dosage form of claim 8 wherein the solid carrier comprises (a) from 70 to 100 percent by weight of a diluent; (b) from 0 to 20 percent by weight of a disintegrant; and (c) 0 to 10 percent by weight of a lubricant.

10. A dosage form of claim 9 wherein the solid carrier comprises (a) from 85 to 97 percent by weight of a diluent;

(b) from 1 to 10 percent by weight of a disintegrant; and (c) 0.2 to 5 percent by weight of a lubricant.

11. A dosage form of claim 10 wherein the solid carrier comprises (a) from 90 to 97 percent by weight of a diluent; (b) from 1 to 5 percent by weight of a disintegrant; and (c) 0.5 to 2 percent by weight of a lubricant.

12. A dosage form of claim 9 wherein the diluent is a monosaccharide, a disaccharide or a polysaccharide.

13. A capsule dosage form of claim 8 wherein the average dissolution at 30 minutes is at least 90 percent of the label amount with no individual capsule below 80 percent of the label amount.

14. A capsule dosage form of claim 13 wherein the average dissolution at 30 minutes is at least 95 percent of an initial average dissolution.

15. A dosage form of claim 13 wherein the solid carrier comprises (a) from 70 to 100 percent by weight of a diluent; (b) from 0 to 10 percent by weight of a disintegrant; and (c) 0 to 10 percent by weight of a lubricant.

16. A method of administering a therapeutically effective amount of terazosin to a human subject, which comprises producing a plasma concentration of terazosirl in the subject having both a maximum concentration ($C_{max}$) and an area under a plasma-concentration vs. time curve (AUC) within the range from −20% to +25% of that produced by a reference liquid-filled terazosin capsule, which contains an equivalent amount of terazosin in a non-aqueous liquid carrier, by administering a solid-filled capsule dosage form which consists essentially of a pharmaceutically effective amount of terazosin in the form of a solid pharmaceutically acceptable salt, or solvate thereof, and a solid carrier to the subject.

17. A method of claim 16 wherein the reference liquid-filled capsule is the subject of approved New Drug Application number N20347.

* * * * *

UNITED STATES PATENT AND TRADEMARK OFFICE
CERTIFICATE OF CORRECTION

PATENT NO. : 5,952,003
DATED      : September 14, 1999
INVENTOR(S) : GUENTENSBERGER ET AL.

It is certified that error appears in the above-identified patent and that said Letters Patent is hereby corrected as shown below:

column 12, claim 16, line 3, the word "terazosirl" is spelled incorrectly. The correct spelling is -- terazosin -- .

Signed and Sealed this

Eleventh Day of April, 2000

Attest:

Q. TODD DICKINSON

*Attesting Officer*      *Director of Patents and Trademarks*